United States Patent
Luan et al.

(10) Patent No.: US 7,283,611 B1
(45) Date of Patent: Oct. 16, 2007

(54) SEGMENTATION ALGORITHMIC APPROACH TO STEP-AND-SHOOT INTENSITY MODULATED RADIATION THERAPY

(75) Inventors: Shuang Luan, Albuquerque, NM (US); Danny Z. Chen, Granger, IN (US); Xiaobo S. Hu, Granger, IN (US); Chao Wang, Mishawaka, IN (US); Xiaodong Wu, Iowa City, IA (US); Cedric X. Yu, Clarksville, MD (US)

(73) Assignee: The University of Notre Dame, Notre Dame, IN (US)

( * ) Notice: Subject to any disclaimer, the term of this patent is extended or adjusted under 35 U.S.C. 154(b) by 183 days.

(21) Appl. No.: 11/085,510

(22) Filed: Mar. 22, 2005

Related U.S. Application Data

(60) Provisional application No. 60/554,902, filed on Mar. 22, 2004.

(51) Int. Cl.
*A61N 5/10* (2006.01)
(52) U.S. Cl. ............................. 378/65; 378/51; 378/64; 378/901
(58) Field of Classification Search ............ 378/51–69, 378/147, 901
See application file for complete search history.

(56) References Cited

U.S. PATENT DOCUMENTS

| | | | | |
|---|---|---|---|---|
| 5,663,999 A | * | 9/1997 | Siochi | 378/65 |
| 6,449,335 B1 | * | 9/2002 | Siochi | 378/65 |
| 6,661,871 B2 | * | 12/2003 | Siochi | 378/65 |
| 6,853,705 B2 | * | 2/2005 | Chang | 378/65 |
| 7,085,348 B2 | * | 8/2006 | Kamath et al. | 378/65 |
| 2003/0068009 A1 | * | 4/2003 | Xing | 378/65 |
| 2004/0066892 A1 | * | 4/2004 | Alber | 378/65 |
| 2004/0071261 A1 | * | 4/2004 | Earl et al. | 378/65 |

OTHER PUBLICATIONS

Chen et al., Geometric Algorithms for Static Leaf Sequencing Problems in Radiation Therapy, Oct. 2004, World Scientific, vol. 14, No. 4-5.*

Luan et al., A New MLC Segmentation Algorithm/Software for Step-and-Shoot IMRT Delivery, Mar. 10, 2004, Med. Phys. vol. 31, No. 4.*

Spezi et al., A DICOM-RT-based Toolbox for the Evaluation and Verification of Radiotherapy Plans, Nov. 12, 2002, Phys. Med. Biol., vol. 47.*

\* cited by examiner

*Primary Examiner*—Courtney Thomas
*Assistant Examiner*—Alexander Taningco
(74) *Attorney, Agent, or Firm*—Jagtiani + Guttag

(57) ABSTRACT

The present invention provides a method comprising recursively partitioning an intensity modulated beam into plateaus; and partitioning the plateaus into segments. The present invention also provides a method for controlling administration of radiation therapy to a patient based on static leaf prescriptions. In addition, the present invention provides a method for partitioning an IMB.

23 Claims, 12 Drawing Sheets

| 1 | 1 | 2 | 2 | 4 | 0 | 2 |
|---|---|---|---|---|---|---|
| 1 | 3 | 2 | 4 | 5 | 2 | 1 |
| 3 | 5 | 3 | 5 | 0 | 0 | 2 |
| 2 | 4 | 0 | 4 | 5 | 0 | 1 |
| 0 | 2 | 0 | 0 | 4 | 2 | 1 |
| 2 | 1 | 2 | 3 | 3 | 0 | 1 |
| 1 | 1 | 0 | 2 | 2 | 0 | 0 |

Prior Art

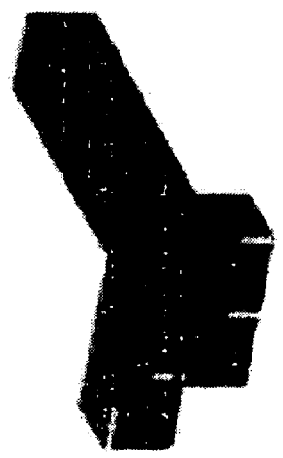
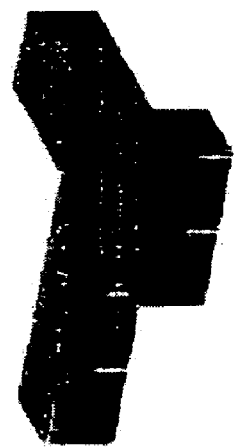
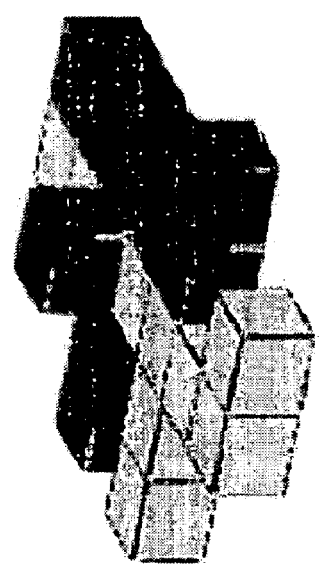

Prior Art

FIG. 5A
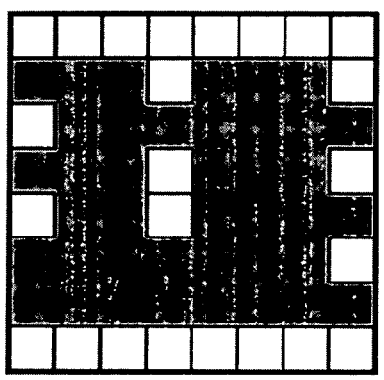
Prior Art
FIG. 5B
| 0 | 1 | 0 | 0 | 0 | 0 | 1 | 1 |
|---|---|---|---|---|---|---|---|
| 7 | 6 | 6 | 3 | 5 | 4 | 4 | 3 |
| 2 | 5 | 4 | 6 | 6 | 5 | 6 | 7 |
| 7 | 6 | 6 | 3 | 6 | 5 | 5 | 3 |
| 3 | 5 | 5 | 3 | 5 | 4 | 4 | 7 |
| 4 | 5 | 5 | 3 | 5 | 5 | 6 | 3 |
| 4 | 4 | 5 | 5 | 5 | 6 | 7 | 6 |
| 0 | 2 | 2 | 3 | 3 | 2 | 1 | 0 |
Prior Art
FIG. 5C
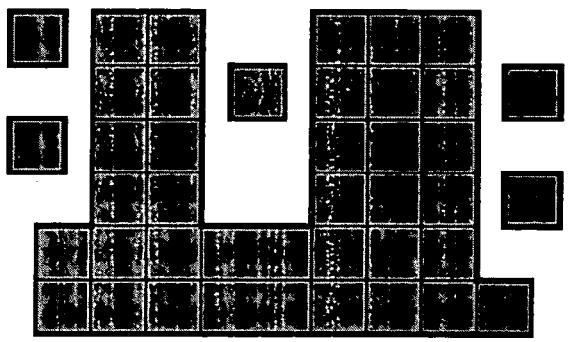
FIG. 5D
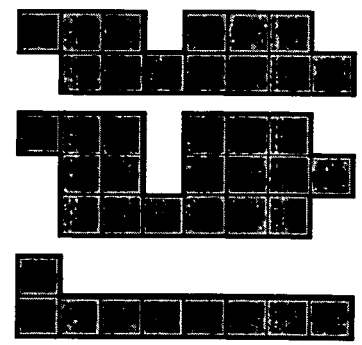
Prior Art

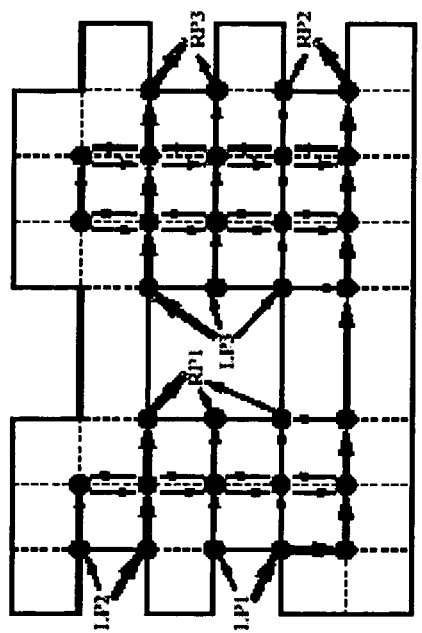
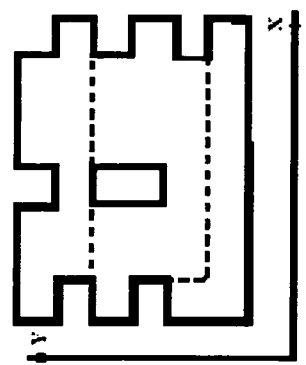
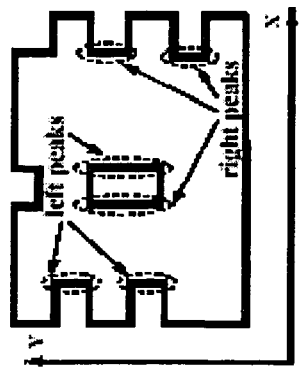
FIG. 6C
FIG. 6B
FIG. 6A

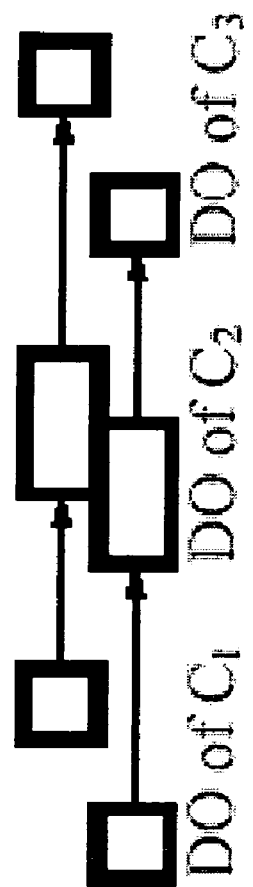

FIG. 9A  FIG. 9B
FIG. 9C
Steiner points
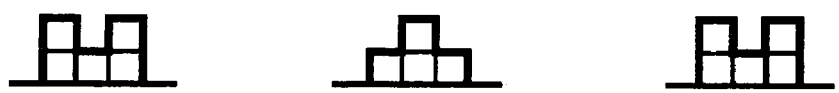
FIG. 9D
FIG. 9E
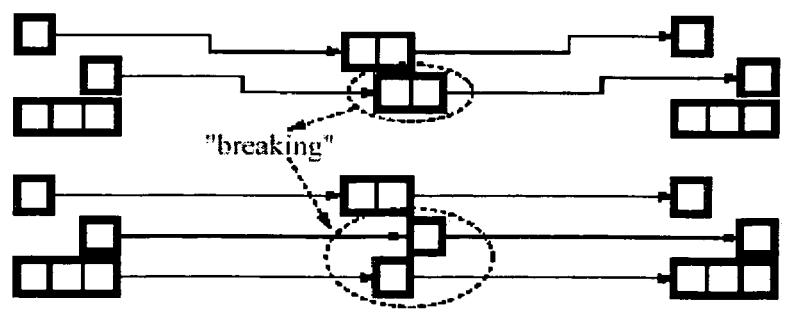
"breaking"

SEGMENTATION ALGORITHMIC APPROACH TO STEP-AND-SHOOT INTENSITY MODULATED RADIATION THERAPY

CROSS-REFERENCE TO RELATED APPLICATIONS

This application makes reference to and claims priority to now abandoned U.S. Provisional Patent Application No. 60/554,902, entitled "Method to Construct Radiation Intensity Distributions Using Uniform Fields for Radiation Therapy," filed Mar. 22, 2004, and to concurrently filed U.S. patent application, entitled "Error Control in Algorithmic Approach to Step-and-Shoot Intensity Modulated Radiation Therapy," the entire contents and disclosure of which is hereby incorporated by reference.

GOVERNMENT INTEREST STATEMENT

The United States Government has rights in this invention pursuant to Grant No. CCR-9988468 with the National Science Foundation.

BACKGROUND

1. Field of the Invention

The present invention relates generally to intensity modulated radiation therapy (IMRT), and more particularly, to a segmentation algorithmic approach to IMRT.

2. Related Art

Intensity Modulated Radiation Therapy (IMRT) is a new technique for cancer treatments and aims to deliver a highly conformal dose to the target volume while keeping the dose to other surrounding organs at risk (OAR) below tolerance levels, see T. R. Bortfeld, A. L. Boyer, W. Schlegel, D. L. Kahler, and T. L. Waldron, Experimental verification of multileaf conformal radiotherapy, In A. R. Hounsell, J. M. Wilkinson, and P. C. Williams, editors, Proc. 11th Int. Conf. on the Use of Computers in Radiation Therapy, pages 180-181, 1994; T. R. Bortfeld, A. L. Boyer, W. Schlegel, D. L. Kahler, and T. L. Waldron, Realization and verification of three-dimensional conformal radiotherapy with modulated fields, Int. J. Radiat. Oncol. Biol. Phys., 30:899-908, 1994; C. S. Chui, T. LoSasso, and S. Spirou, Dose calculation for photon beam with intensity modulation generated by dynamic jaw or multileaf collimation, Med. Phys., 21:1237-1244, 1994; P. Geis, A. L. Boyer, and N. H. Wells, Use of a multi-leaf collimator as a dynamic missing-tissue compensator, Med. Phys., 23:1199, 1996; C. C. Ling, C. Burman, S. Chui, G. J. Kutcher, S. A. Leibel, T. LoSasso, R. Mohan, T. Bortfeld, L. Reistein, S. Spirou, X. H. Wang, Q. Wu, M. Zelefsky, and Z. Fuks, Conformal radiation treatment of prostate cancer using inverse-planned intensity modulated photon beams produced with dynamic leaf collimation, Int. J. Radiat. Oncol. Biol. Phys., 35:721-730, 1996; X. Wang, S. Spirou, T. LoSasso, J. Stein, C. S. Chui, and R. Mohan, Dosimetric verification of intensity-modulated field, Med. Phys., 23:317-327, 1996; S. Webb, The Physics of Three-Dimensional Radiation Therapy, Bristol, IoP Publishing, 1993; K. R. Winston and W. Lutz, Linear accelerator as a neurosurgical tool for stereotactic radiosurgery, Neurosurgery, 22(3):454-464, 1988; and $C_{max}$. Yu, M. J. Symons, M. N. Du, A. A. Martinez, and J. W. Wong, A method for implementing dynamic intensity modulation using independent jaws and a multileaf collimator, Phys. Med. Biol., 40:769-787, 1995, the entire contents and disclosures of which are hereby incorporated by reference. Implementation of IMRT requires an ability to deliver 2-dimensional non-uniform fluence distributions, called intensity maps or intensity modulated beams (IMBs) (see FIG. 1A).

Currently, IMRT may be delivered by multiple overlapping fields shaped by a multileaf collimator (MLC), (see FIG. 1B for a schematic representation of an MLC), see also T. J. Jordan and P. C. Williams, The design and performance characteristics of a multileaf collimator, Phys. Med. Biol., 39:231-251, 1994, the entire contents and disclosure of which is hereby incorporated by reference. Using a MLC, IMRT may be implemented either statically or dynamically. In dynamic approaches, the MLC leaves keep moving across a treatment field while the radiation remains on. In static approaches, also referred to as "step-and-shoot" IMRT, the MLC leaves stay stationary during irradiation, and move to reshape the beam while the radiation is turned off. A number of dynamic and static MLC techniques have been described previously, see S. Webb, The Physics of Three-Dimensional Radiation Therapy, Bristol, IoP Publishing, 1993; and S. Webb, The Physics of Conformal Radiotherapy, Advances in Technology, Bristol, IoP Publishing, 1997, the entire contents and disclosures of which are hereby incorporated by reference.

Due to the complexity of dynamic intensity modulated beams, the verification of all aspects of the planning and delivery procedures becomes difficult. Thus, "step-and-shoot" is the currently preferred method for delivering IMRT in clinical practices. Advantages of the "step-and-shoot" technique include precise delivery, easy verification, and general availability. A key disadvantage, however, is that it may require a prolonged treatment time, since radiation has to be constantly switched on and off to allow MLC leaves to reshape. In some machines, such as those commercially available from ELEKTA INC., and SIEMENS Corporation, the inter-segment delay dominates the total treatment time in a step-and-shoot delivery. Thus, in such cases, it is highly desirable to use a leaf sequence with the fewest segments possible to deliver the desired intensity map, P. Xia and L. J. Verhey, MLC leaf sequencing algorithm for intensity modulated beams with multiple static segments, Medical Physics, 25:1424-1434, 1998, the entire contents and disclosure of which is hereby incorporated by reference.

SUMMARY

According to a first broad aspect of the present invention, there is provided a, method comprising the following steps: (a) recursively partitioning an intensity modulated beam into plateaus; and (b) partitioning the plateaus into segments.

According to a second broad aspect of the invention, there is provided a method comprising the following steps: (a) determining static leaf sequencing segments for a plurality of intensity modulating beams; (b) determining monitor units based on the static leaf sequencing segments; (c) determining static leaf sequencing prescriptions based on prescription data and the monitor units determined in step (b); and (d) controlling administration of radiation therapy to a patient based on the static leaf prescriptions.

According to a third broad aspect of the invention, there is provided a method comprising the following steps: (a) constructing a directed graph based on a zero-one IMB; (b) determining a maximum flow in the directed graph; and (c) extracting the segments from the directed graph based on the maximum flow determined in step (b) to thereby partition the zero-one IMB.

According to a fourth broad aspect of the invention, there is provided a method comprising the following steps: (a) generating a canonical delivery option for each set of field opening endpoints for a plurality of intensity modulated beam columns of an IMB; (b) for every two consecutive intensity modulated beam columns, determining a maximum matching between the canonical delivery options of the intensity modulated beam columns; and (c) extracting the segments for the IMB based on the matched field openings of the canonical delivery options in an increasing order of consecutive intensity modulated beam columns to thereby partition the IMB.

BRIEF DESCRIPTION OF THE DRAWINGS

The invention will be described in conjunction with the accompanying drawings, in which:

FIG. 3A is perspective view of a segment corresponding to an MLC aperture in accordance with an embodiment of the present invention;

FIG. 3B is perspective view of a segment corresponding to an MLC aperture in accordance with an embodiment of the present invention;

FIG. 3C is a perspective view of the segment in 3B being placed on top of the segment of 3A, so that some of the unit cubes of the segment one in 3B drop to the first layer, where the light cells represent the segment of FIG. 3A and the dark cells represent the segment in FIG. 3B;

FIG. 5A shows an IMB with entries of either 0 (blank) or 1 (shaded);

FIG. 5B shows an IMB, where the shaded area denotes entries $\geq 4$;

FIG. 5C shows the output of a sliding window-like method for the 2-D segmentation problem on the shaded area (6 mLC aperture shapes, assuming the MLC leaves are moving along the y-axis), with some of the cells in 5C stretched for the sake of clarity;

FIG. 5D shows the optimal output of a 2-D segmentation algorithm (3 mLC aperture shapes) in accordance with an embodiment of the present invention;

FIG. 6A is a schematic diagram of a polygon showing the left and right peaks of the polygon;

FIG. 6B is a schematic diagram of the polygon of FIG. 6A showing that the three dividing curves (dashed) yield an optimal segmentation of the polygon;

FIG. 6C shows the directed grid graph modeling the 2-D segmentation problem for the polygon of FIGS. 6A and 6B in which the thick edges indicate a maximum flow;

FIG. 7A shows a simple IMB in accordance with an embodiment of the present invention;

FIG. 7B is a diagram showing that the IMB in FIG. 7A may be partitioned into 2 segments of a unit height (assuming the MLC leaves move along the y-axis);

FIG. 7C shows the intensity profiles (IP) of the 3 columns of the IMB in FIG. 7A;

FIG. 7D is a diagram showing the delivery options (DO) of the 3 intensity profiles in FIG. 7C and the stitching of their field openings (indicated by arrows), where each path following the arrows corresponds to a segment in FIG. 7B;

FIG. 9A shows an IMB in accordance with an embodiment of the present invention;

FIG. 9B is a diagram showing an optimal solution in accordance with an embodiment of the present invention without using Steiner points;

FIG. 9C is a diagram showing the 3 segments for an optimal solution in accordance with an embodiment of the present invention using Steiner points;

FIG. 9D shows the intensity profiles (IP) of the 3 columns of the IMB in FIG. 9A;

FIG. 9E is a diagram showing the delivery options (DO) of the 3 intensity profiles in FIG. 9D and the stitching of their field openings (indicated by arrows), where each path following the arrows corresponds to a segment in FIG. 9C;

FIG. 12C showing the overlay of the isodose lines of 75% and 40% in FIGS. 12A and 12B.

DETAILED DESCRIPTION

Figures 1A, 1B:
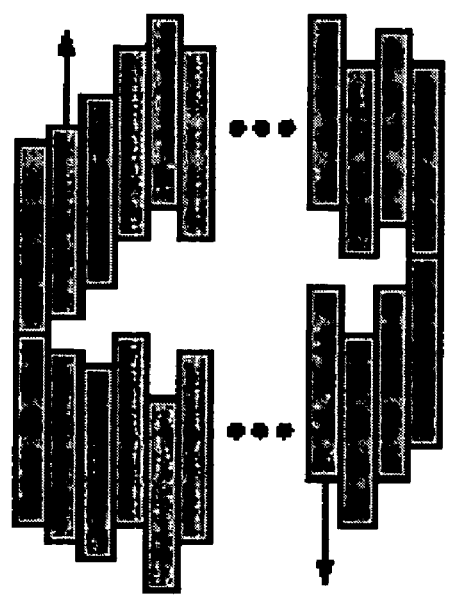
FIG. 1A is a charting showing a sample intensity modulated beam (IMB) to be delivered by a sequence of MLC shapes.
FIG. 1B shows in schematic form the projection of an MLC aperture shape on the isocentric plane.
Figure 2A:
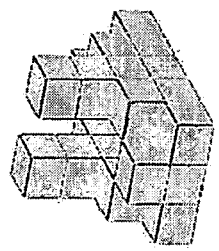
FIG. 2A is perspective view of a 3-D IMB mountain and the corresponding intensity map in accordance with an embodiment of the present invention.
Figure 2B:
FIGS. 2B, 2C, 2D and 2E are perspective views of four plateaus (segments) of a unit height for building the 3-D IMB mountain of FIG. 2A in accordance with an embodiment of the present invention.
Figure 2C:
Figure 2D:
Figure 2E:

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, a value or property is "based" on a particular value, property, the satisfaction of a condition, or other factor, if that value is derived by performing a mathematical calculation or logical decision using that value, property or other factor.

For the purposes of the present invention, the term "multileaf collimator" or "MLC" refers to a device for delivering intensity modulated beams consisting of multiple pairs of tungsten leaves of the same rectangular shape and size.

Opposite MLC leaves of every pair are aligned to each other. The leaves may move up and down to form a rectilinear polygonal region that is monotone to, for example, the x-axis.

For the purposes of the present invention, the term "segment" refers to an MLC-aperture shape formed by MLC leaves, together with intensity levels, which are delivered by the MLC-aperture.

For the purposes of the present invention, the term "segmentation algorithm" refers generally to an algorithm that finds a minimum number of segments that creates a given intensity-modulated beam (IMB).

For the purposes of the present invention, the term "graph" refers to a discrete data structure used to model complex relationships among objects and consists of vertices and edges connecting the vertices.

For the purposes of the present invention, the term "bipartite graph" refers to a graph whose vertex set consists of two disjoint sub-sets of vertices U and V, such that all the edges only connects the vertices from U to the vertices V.

For the purposes of the present invention, the term "bipartite matching" refers to a set of edges in a bipartite graph such that no two edges share a common vertex.

For the purposes of the present invention, the term "bipartite maximum matching" refers to a bipartite matching with the most number of edges.

For the purposes of the present invention, the term "graph algorithm techniques" refers to techniques and methods that use graph data structures to model and solve problems.

For the purposes of the present invention, a "bipartite maximum matching algorithm" refers to a method for computing a bipartite maximum matching for a bipartite graph.

For the purposes of the present invention, the term "intensity map" refers to an intensity-modulated beam (IMB).

For the purposes of the present invention, the term "intensity modulated beams" or "IMB" refers to the prescribed discrete fluence distributions of radiation. An IMB along a given direction in 3-D is specified by a set of nonnegative integers on a 2-D grid.

For the purposes of the present invention, the term "IMB column" refers to a column of the matrix that corresponds to an IMB.

For the purposes of the present invention, the term "intensity profile" refers to a row of the matrix that corresponds to an IMB.

For the purposes of the present invention, when referring to a grid cell, the term "intensity level" refers to the number in the grid cell which correlates to the amount (in unit) of radiation to be delivered by the IMB to the body region corresponding to that cell.

For the purposes of the present invention, the term "leaf sequence" refers to a set of segments that creates a given set of IMBs.

For the purposes of the present invention, the term "shortest-path algorithm" refers to: A path in a graph from vertex $v_1$ to $v_k$ is a sequence of vertices $v_1, v_2, \ldots, v_k$ that are connected by the edges $(v_1, V_2), (V_2, V_3), \ldots, (V_{k-1}, V_k)$. (The edges are also considered to be part of the path.) When the each edge in the graph has a cost (a real number) that is associated with it, the graph is said to be a weighted graph. The cost of a path in a weighted graph is the total sum of its edge costs. A shortest path between two vertices u and v of a weighted graph is a path between u and v with the minimum cost. A shortest path algorithm is a method for finding a shortest path between two vertices in a weighted graph.

For the purposes of the present invention, the term "maximum-flow algorithm" refers to: A graph is called a network if: (1) it is directed, i.e., for any two vertex u and v, the edge (u,v) and (v,u) is different, the edge (u,v) is said to be entering v and exiting u; (2) there are two distinct vertices, the source vertex s and the sink vertex t where there is no edge entering s and there is no edge exiting t; and (3) each edge has a capacity that is a positive number. A flow is a function f on the edges of a network that satisfies the following two condition: (1) for any edge e, f(e) is less than the capacity of e and (2) for any vertex v that is neither s nor t, the total flow entering it, i.e., the sum of the flow values on the edges directing at v, is equal to the total flow exiting v, i.e., the sum of the flow values on the edges exiting v. The value of a flow function f is the total flow values on the edges exiting the source vertex s. A flow function f is a maximum flow, if the value of the flow function is the maximum among all the flow functions. A maximum-flow algorithm is a method for finding a maximum flow on a network.

For the purposes of the present invention, the term "mixed partitioning scheme" refers to a way to partition an IMB into sub-IMBs using more than one partitioning method in a dynamic programming fashion.

For the purposes of the present invention, the term "step-and-shoot" refers to a static IMRT method in which the MLC leaves stay stationary during irradiation, and move to reshape the beam while the radiation is turned off.

For the purposes of the present invention the term "sub-IMB" refers to a portion of an IMB.

For the purposes of the present invention, the term "plateau" refers to sub-IMB having a height of 0 or d, where d is a positive number less than the height of the IMB of which the sub-IMB is a portion.

For the purposes of the present invention, the term "mutually disjoint" refers to two geometric curves that do not intersect each other.

For the purposes of the present invention, the term "canonical delivery option" refers to: A delivery option of an intensity profile is a set of field-openings (FOs) together with an intensity level of one that created it. Mathematically, each field-opening can be viewed as a closed interval on the real line [1, r]. Hence a delivery option can be viewed as a set of intervals on the real line, e.g., $[1_1, r_1], [1_2, r_2], \ldots, [1_k, r_k]$. A delivery option is canonical if none of its interval is strictly contained in the interior of another interval of it For the purposes of the present invention, the term "FO-endpoint" refers to a field opening endpoint. Mathematically, a field-opening can be viewed as a closed interval [1, r] on the real line. The FO-end point refers to the numbers 1 and r.

For the purposes of the present invention, the term "Steiner point" refers to a way in which a field-opening [1, r] is split into two new field openings [1,x] and [x,r], with 1<x<r.

For the purposes of the present invention, the term "z-post" refers to intensity level of each grid cell of an IMB.

DESCRIPTION

The present invention provides an MLC (multileaf collimator) segmentation algorithm and software for step-and-shoot IMRT (intensity modulated radiation therapy) delivery. The present invention shortens treatment time by minimizing the number of segments that are utilized. According to an embodiment of the present invention, a segmentation algorithm is provided, referred to herein as SLS (static leaf sequencing), which is based on graph algorithmic techniques.

A key measure of IMRT is the total delivery time for an IMB, because minimizing the total delivery time not only lowers the treatment cost but also improves its effect. Since the overhead associated with turning the beam source on and off, repositioning MLC leaves, and the required verifications dominate the total delivery time, it is highly desirable to minimize the number of MLC-shaped regions used for delivering each IMB.

SLS takes advantage of the geometry of intensity maps. According to an embodiment of the present invention, the treatment times of IMRT plans are shortened by significantly reducing the number of aperture shapes used. The input to SLS is intensity maps computed by planning systems, and the output is optimized leaf sequences.

In an SLS approach of the present invention, intensity maps may be viewed as 3-dimensional (3-D) mountains made of, for example, unit-sized cubes. Such a 3-D mountain may be first partitioned into special-structured sub-mountains using a mixed partitioning scheme. Then, the optimal leaf sequences for each sub-mountain may be computed by either a shortest-path algorithm or a maximum-flow algorithm based on graph models. The computations of SLS take only a few minutes. Treating an intensity map as a 3-dimensional solid has also been considered by Siochi; however, his "rod pushing" algorithm is not based on graph algorithmic techniques, see R.A.C. Siochi, Minimizing static intensity modulation delivery time using an intensity solid paradigm, Int. J. Radiation Oncology Biol. Phys., 43(3):671-680, 1999, the entire contents and disclosure of which is hereby incorporated by reference.

An embodiment of the present invention also provides an SLS software package using C programming language on Linux workstations. It should be appreciated that any programming language or hardware implementation system that utilizes the techniques of the present invention is within the scope of the present invention. Comparison studies of SLS with both the 4.0 and 5.0 versions of CORVUS (a popular commercial planning system developed by NOMOS Corp.) and with Xia and Verhey's segmentation methods on ELEKTA linac systems showed substantial improvements, see P. Xia and L. J. Verhey, MLC leaf sequencing algorithm for intensity modulated beams with multiple static segments, Medical Physics, 25:1424-1434, 1998, the entire contents and disclosure of which is hereby incorporated by reference. The comparisons between SLS and CORVUS indicate that for the same intensity maps, the number of aperture shapes computed by SLS are up to 80% less than CORVUS 4.0 and 40% less than CORVUS 5.0 (31% less than CORVUS 5.0 with the leakage correction turned off) on ELEKTA linac systems. Analysis based on software simulations, delivered films, and ion chamber measurements showed that the 3-D doses produced by modified IMRT plans of SLS match those of CORVUS, and thus confirmed the clinical feasibility of SLS. The comparisons between SLS and Xia and Verhey's algorithm also showed significant improvements by the present invention. For the same set of intensity maps under the ELEKTA constraints, SLS outperformed Xia and Verhey's algorithm by about 33% in terms of the number of aperture shapes. For instance, for a pancreatic case, SLS used only ⅕ of the number of segments required by CORVUS 4.0 to create the same intensity maps, and the SLS sequences took only 25 minutes to deliver on an ELEKTA SL 20 linac system in contrast to the 72 minutes for the CORVUS 4.0 sequences (a 3-fold improvement). SLS may also be extended to other types of linac systems.

A goal of an MLC segmentation algorithm is to generate a minimum number of aperture shapes or segments for creating a desired intensity map. While most known approaches formulate the problem as a matrix partition problem, i.e., partitioning the intensity map matrix into a set of special matrices each defining an aperture shape, the approach of the present invention is very different in that it exploits the geometric nature of the problem.

Geometrically, one may view an MLC aperture shape as a polygon on the xy-plane which also has a uniform "height" in the z-axis; the height of the polygon represents the radiation intensity to be delivered for that aperture shape. In this view, each aperture shape may be treated as a plateau in the 3-D space with a uniform height h for some integer h>0, see FIGS. 2B, 2C, 2D and 2E. Hence, intuitively, one may view the segmentation problem in step-and-shoot delivery as playing the following game: A given IMB (intensity map) is a 3-D mountain made of unit-sized cubes, e.g., FIG. 2A, and one seeks to build this mountain by stacking up the minimum number of plateaus (segments) as illustrated in FIGS. 2A, 2C, 2D and 2E. It is important to note that each plateau used, like the 3-D IMB mountain, is not one whole rigid object, i.e. it is made of unit cubes as well. Thus, when two segments are stacked together, some of the cubes may fall to lower positions as if they are pulled down by gravity, see FIGS. 3A, 3B and 3C for illustrations.

Figure 4:
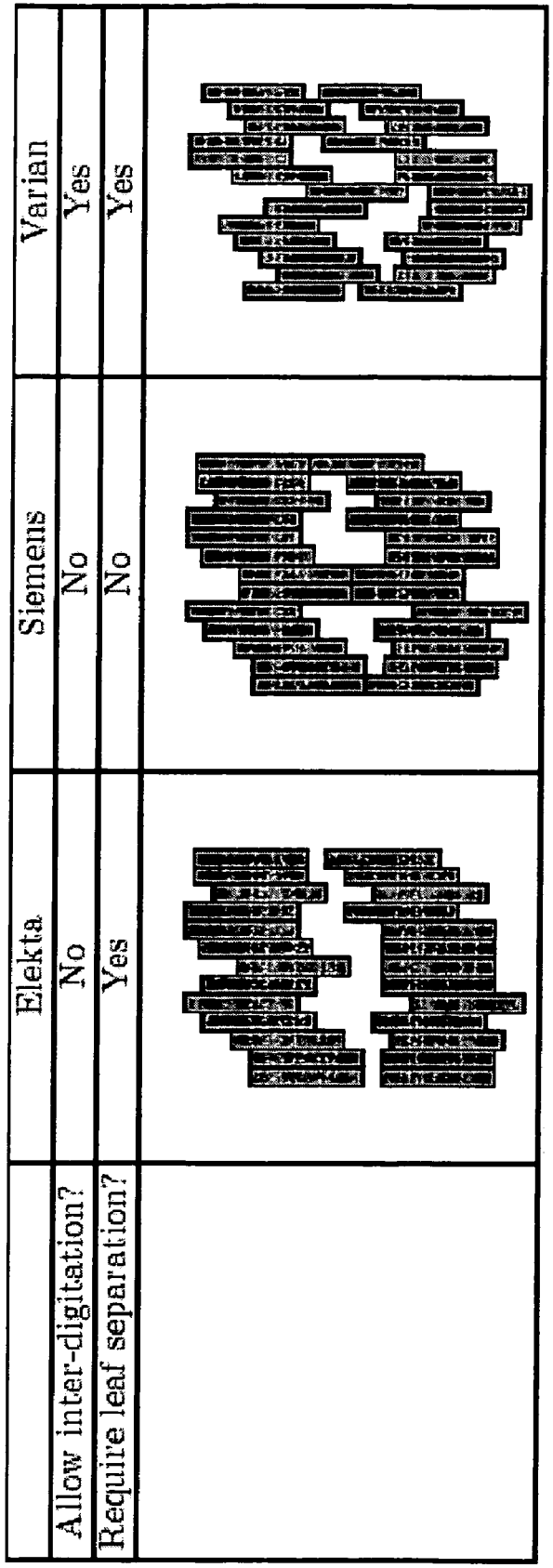
FIG. 4 is a diagram showing the constraints of several popular linac systems.

Geometrically, a goal of the present invention is to partition a 3-D IMB mountain into the minimum number of plateaus (segments) of uniform heights. Since these plateaus are defined by an MLC aperture shape, i.e., the cross-section of a plateau on the xy-plane corresponds to an MLC aperture shape, the mechanical constraints of the MLC preclude certain plateaus from being used to build the IMB mountains, see D. J. Convery and S. Webb, Generation of discrete beam-intensity modulation by dynamic multileaf collimation under minimum leaf separation constraints, Phys. Med. Biol., 43:2521-2538, 1998; and T. J. Jordan and P. C. Williams, The design and performance characteristics of a multileaf collimator, Phys. Med. Biol., 39:231-251, 1994, the entire contents and disclosures of which are hereby incorporated by reference. One such constraint is called minimum leaf separation, e.g., on an ELEKTA or VARIAN linac system, which requires the distance between the two opposite leaves of any MLC leaf pair to be no smaller than a given value $\delta$ (e.g., $\delta$=1 cm). Another common constraint is called no interdigitation, e.g., on an ELEKTA or SIEMENS linac system, which forbids the leaf tip of each MLC leaf to surpass its neighboring leaves on the opposing leaf bank. These constraints prevent opposite MLC leaves from colliding into each other and being damaged. FIG. 4 illustrates these constraints on the popular clinical linac systems.

In the present invention, the ELEKTA MLC constraints are primarily addressed; however, it is possible to extend the approach of the present invention to other linac collimator systems and is considered within the teachings of the present invention.

Embodiments of the present invention may be used to solve three versions of the segmentation problem. These problems are:

1. The 2-D segmentation problem: Given an IMB with entries of either 0 or 1 (called zero-one IMB), find the minimum number of segments for creating the IMB, such that each segment has a height of 1. FIG. 5A provides an example of a zero-one IMB;

2. The Basic SLS segmentation problem: Given an arbitrary IMB, find the minimum number of segments for the IMB, such that each segment has one unit of intensity. FIGS. 2A, 2B, 2C, 2D and 2E provide an example of the Basic SLS segmentation problem; and 3. The 3-D segmentation problem: Given an arbitrary IMB, find the minimum number of segments for the IMB, such that each segment has an arbitrary integral intensity level.

It should be noted that both the 2-D segmentation problem and the Basic SLS segmentation problem are special cases of the 3-D segmentation problem.

In the solution of the present invention for the 3-D segmentation problem, the 2-D segmentation problem and the Basic SLS segmentation problem are first optimally solved. Here, the word "optimal" means that the optimal output quality of the solutions for these special cases may be proved mathematically. Then, based on the optimal solutions for the special cases, the present invention presents an effective segmentation algorithm for the 3-D segmentation problem.

The first special case of the 3-D segmentation problem considered herein is the 2-D segmentation problem, e.g., see FIGS. 5A, 5B, 5C and 5D: Given a zero-one IMB (with entries of either 0 or 1), find the minimum number of segments for creating the zero-one IMB, such that each segment has a height of 1. This 2-D version may be viewed as a polygon partition problem that seeks to partition a given planar domain into the minimum number of desired polygons; here, each resulting polygon corresponds to an MLC aperture shape.

The 2-D segmentation problem is important in that an optimal solution for this problem may lead to potential improvements to the segmentation algorithm introduced by Xia and Verhey. To illustrate the importance of this 2-D problem, the main ideas of Xia and Verhey's algorithm should be reviewed. The following are the major steps of their algorithm based on the "reducing level" technique used in the Galvin et al. paper, see J. M. Galvin, X. G. Chen, and R. M. Smith, Combining multileaf field to modulate fluence distribution, Int. J. Radiat. Oncol. Biol. Phys., 27:697-705, 1993, the entire contents and disclosure of which is hereby incorporated by reference:

1. Choose an intensity level $d=2^i$, where $i=\text{Int}(\log_2(I_{max}))-1$ (for any value $I>1$, $\text{Int}(\log_2(I))$ denotes the power of 2 closest to I) and $I_{max}$ is the maximum intensity level of the IMB under consideration.

2. From the IMB, find an aperture shape with the largest area on the xy-plane and with an intensity level d; remove this aperture shape from the IMB. It should be noted that the algorithm by Xia and Verhey was mainly designed to address the SIEMENS constraints. Hence, to adapt their algorithm to satisfy the ELEKTA constraints, one needs to find the largest aperture shape subject to the ELEKTA constraints in this step.

3. Repeat Steps 1 and 2 on the remaining IMB, until the remaining IMB is empty.

For example, on the IMB in FIG. 5B, the maximum intensity level $I_{max}=7$, $i=\text{Int}(\log_2(I_{max}))-1=2$, and $d=2^i=4$. If one keeps applying the above algorithm to segment the IMB in FIG. 5B until $I_{max}$ is no longer 7, then this segmentation process produces the segments in FIG. 5C, all having a height of d=4. For the purposes of this description, it may be assumed that the MLC leaves always move along the y-axis. This is not always the case, and thus the parameter may be adjusted in accordance with the teachings of the present invention.

Observe that in the above segmentation process, Xia and Verhey's algorithm essentially performs a partition of the shaded area in FIG. 5B, i.e., containing all entries whose values are at least 4. In FIG. 5B, if one views the shaded area as containing entries which are all marked by 1 and the unshaded areas as containing entries marked by zero, then Xia and Verhey's algorithm is in fact dealing with the 2-D segmentation problem (partitioning the shaded area in FIG. 5A). Thus, the 2-D segmentation problem arises as a key subproblem in Xia and Verhey's algorithm.

In Xia and Verhey's algorithm, a "sliding window"—like method is used to solve the 2-D segmentation problem, which repeatedly finds the largest-area deliverable aperture shapes. Applying the sliding window method to the shaded area in FIG. 5A generates 6 aperture shapes, each with a height of 4 (FIG. 5C), while the mathematically optimal solution produced by an algorithm according to an embodiment of the present invention has only 3 aperture shapes (FIG. 5D), cutting down the number of aperture shapes by 50% for this example.

According to an embodiment of the present invention, there is provided an optimal 2-D segmentation algorithm, called 2-D SLS. The key idea of 2-D SLS is based on an observation called peak eliminations. For convenience, hereafter in this section, the present invention refers to any zero-one IMB as a polygon P on the xy-plane. Note that such a polygon P may contain holes and the boundary edges of P are either vertical or horizontal. A vertical boundary edge e of a polygon P is referred to as a left peak if the two horizontal edges of P adjacent to e are both to the left of e (see FIG. 6A). Similarly, a right peak is a vertical edge of P whose two adjacent horizontal edges are both to its right.

Observe that the existence of left and right peaks is the reason for which the polygon P cannot be delivered by using a single MLC aperture shape. This is because when delivering an MLC aperture shape, each pair of MLC leaves defines an opening of the shape as a continuous vertical strip for the exposure of radiation. Left and right peaks separate the involved vertical strips of the IMB into disjoint pieces, and hence prevent the IMB from being delivered as a single aperture shape. Thus, the key to segmenting P into MLC aperture shapes is to eliminate all left and right peaks by partitioning P into multiple "nice" polygons, i.e., MLC aperture shapes.

For example, to eliminate a left peak e, one must divide P into two smaller polygons using a polygonal curve that connects the peak e to some point p on the boundary of P, such that p is not to the left of e (FIG. 6B). The alternate holds true for a right peak. Such polygonal curves used in partitioning P may be referred to as the dividing curves. Each dividing curve should be deliverable by MLC leaves, that is, it should consist of edges that are only vertical or horizontal, and the widths of the horizontal edges should fit the width of the MLC leaves. Further, a dividing curve should not introduce new left and right peaks; hence, starting at the left end of the curve and walking along the curve, one should always go rightwards and never go leftwards, i.e., the curve is from left to right, with possible ups and downs.

Introducing a dividing curve to eliminate a peak of P may increase the number of resulting polygons (MLC aperture shapes). Hence, to partition P into the minimum number of aperture shapes, the minimum number of dividing curves should be introduced. Since each left or right peak may be eliminated by one dividing curve, and one dividing curve may at best eliminate two peaks, i.e., connecting a left peak to a right peak, it follows that one needs to find a maximum set of mutually disjoint dividing curves such that each curve connects a left peak and a right peak (see FIG. 6B). Note that the dividing curves should be mutually disjoint to avoid introducing redundant aperture shapes. In fact, finding a maximum set of such dividing curves is the key to solving the 2-D segmentation problem. For the remaining unconnected peaks, it is relatively easy to eliminate them by connecting each of them to some non-peak boundary point of P.

To compute a maximum set of connections between the left and right peaks, the task is formulated as a maximum flow problem on a directed grid graph induced by the IMB grid (FIG. 6C). For descriptions on the maximum flow problem and its solutions, see T. H. Cormen, C. E. Leiserson, and R. L. Rivest, Introduction to Algorithms, pages 916-963, McGraw-Hill, 1998, the entire contents and disclosure of which is hereby incorporated by reference. Specifically, we assign a unit flow capacity to all vertices and edges of the grid graph (to be defined below). It may be proved that a maximum flow in this directed grid graph yields a maximum set of desired connections that specifies an optimal solution for the 2-D segmentation problem.

According to an embodiment of the present invention, the main steps of a 2-D SLS algorithm are as follows:

1. Construct a directed graph G induced by the underlying grid of the given zero-one IMB. The vertices of G include all intersection points of the IMB grid that are either part of a peak or in the interior of the polygon P corresponding to the IMB. The edges of G include those edges of the IMB grid whose end points are vertices in G. Directions are assigned to the edges of G based on the following rules:

(a) For an edge involving a left peak vertex, its direction is away from the left peak;

(b) For an edge involving a right peak vertex, its direction is toward the right peak;

(c) The direction of a horizontal edge that does not involve any peak vertex is from left to right; and (d) The direction of a vertical edge that does not involve any peak vertex is bidirectional.

2. For all vertices corresponding to the same left (resp., right) peak, introduce a source (resp., sink) vertex to G, and edges from the source vertex (resp., peak vertices) to those peak vertices (resp., the sink vertex) (see FIG. 6C)).

3. Assign a unit flow capacity to each vertex and edge of G. Note that this flow capacity assignment ensures that any directed path of a unit flow from a source vertex to a sink vertex in G always connects a left peak to a right peak of P.

4. Compute a maximum flow in the directed grid graph G from the source vertices to the sink vertices, and based on the resulting maximum flow, extract the connections between the left and right peaks of P.

5. Eliminate the remaining unconnected peaks, and extract the resulting segments.

Observe that a unit flow capacity on each vertex and edge of G guarantees that a maximum flow in G yields a maximum set of mutually disjoint paths (from the sources to the sinks), which specifies precisely a maximum set of desired connections between the left and right peaks of P. It may be proved that the above 2-D SLS algorithm takes a polynomial time to solve the 2-D segmentation problem.

Another key special case of the 3-D MLC segmentation problem is the Basic SLS segmentation problem, see T. R. Bortfeld, A. L. Boyer, W. Schlegel, D. L. Kahler, and T. L. Waldron, Experimental verification of multileaf conformal radiotherapy, In A. R. Hounsell, J. M. Wilkinson, and P. C. Williams, editors, Proc. 11th Int. Conf. on the Use of Computers in Radiation Therapy, pages 180-181, 1994; T. R. Bortfeld, A. L. Boyer, W. Schlegel, D. L. Kahler, and T. L. Waldron, Realization and verification of three-dimensional conformal radiotherapy with modulated fields, Int. J. Radiat. Oncol. Biol. Phys., 30:899-908, 1994; T. R. Bortfeld, D. L. Kahler, T. J. Waldron, and A. L. Boyer. X-ray field compensation with multileaf collimators, Int. J. Radiat. Oncol. Biol. Phys., 28:723-730, 1994; T. R. Bortfeld, J. Stein, K. Preiser, and K. Hartwig, Intensity modulation for optimized conformal therapy, In Proc. Symp. Principles and Practice of 3-D Radiation Treatment Planning, 1996; A. L. Boyer. Use of MLC for intensity modulation, Med. Phys., 21:1007, 1994; and A. L. Boyer, T. R. Bortfeld, D. L. Kahler, and T. J. Waldron, MLC modulation of x-ray beams in discrete steps, In Proc. 11th Int. Conf. on the Use of Computers in Radiation Therapy, pages 178-179, 1994, the entire contents and disclosures of which are hereby incorporated by reference. Given an arbitrary IMB, find a minimum set of segments for creating that IMB, such that each segment has exactly one unit of intensity. Geometrically, the basic SLS segmentation problem aims to partition a given 3-D IMB mountain into plateaus (segments) of a unit height (see FIGS. 2A, 2B, 2C, 2D and 2E). Note that for the general 3-D segmentation problem, the uniform height of each segment may be any integer $\geq 1$, e.g., in Xia and Verhey's algorithm. Unless otherwise specified, for the purposes of description in this section, all segments are of a unit height. However, according to other embodiments of the present invention, segments may be other than unit height.

Studying the Basic SLS segmentation problem is important because the maximum heights of the majority of IMBs used in current clinical treatments are about 5 to 10 and because a mathematically optimal solution for this special case on such IMBs is often very close to an optimal solution for the general 3-D segmentation problem.

Geometrically, one may view a 3-D IMB mountain as consisting of a series of IMB mountain slices, each of which is a 2-D object defined on a column of the IMB grid (see FIG. 7c for examples of IMB mountain slices). Actually, such an IMB mountain slice corresponds to the concept of an intensity profile or 1-D IMB, see S. Luan, D. Z. Chen, L. Zhang, X. Wu, and C.X. Yu, An optimal algorithm for configuring delivery options of a one-dimensional intensity-modulated beam, Phys. Med. Biol., 48(15):2321-2338, 2003; S. Webb, Configuration options for intensity-modulated radiation therapy using multiple static fields shaped by a multileaf collimator, Phys. Med. Biol., 43:241-260, 1998; and $C_{max}$. Yu, Intensity-modulated arc therapy with dynamic multileaf collimation: An alternative to tomotherapy, Phys. Med. Biol., 40:1435-1449, 1995, the entire contents and disclosure of which is hereby incorporated by reference.

Let $S=\{S_i|i\in I\}$ denote a set of segments that builds a 3-D IMB mountain, where I is an index set. For the Bortfeld-Boyer segmentation problem, since the height of each segment $S_i$ is 1, $S_i$ in fact builds a continuous block of a unit height on every IMB column $C_j$ that intersects the projection of $S_i$ on the IMB grid. The continuous block on an IMB column $C_j$ created by a segment $S_i$ is referred to as a field opening and denoted by $B_{ij}$. Note that when delivering a segment $S_i$, each of its field openings $B_{ij}$ is delivered by a pair of MLC leaves that is aligned to its corresponding IMB column $C_j$.

Suppose that one collects the field openings created by all segments in $\{S_i|i\in I\}$ on an IMB column $C_j$. Then this collection $\{B_{ij}|i\in I\}$ of field openings actually builds the IMB mountain slice (intensity profile) defined on $C_j$. A collection of field openings that builds an IMB mountain slice defined on an IMB column is called a delivery option of the corresponding intensity profile. For example, the boxes of the delivery options in FIG. 7D represent the field openings.

From the above analysis, one may solve the Basic SLS segmentation problem by first selecting a good delivery option for building each IMB mountain slice, and then stitching together the field openings along the consecutive IMB columns to form segments. Here, stitching refers to which of the selected field openings for column $C_j$ should follow which field opening for column $C_j+1$ in a segment (see FIG. 7D). Observe that, if no stitching occurs, a given 3-D IMB mountain may be built by letting each selected field opening be a segment. For example, the IMB in FIG. 7A may be delivered using 6 segments, with each segment being one of the field openings in FIG. 7D. Observe that each time two field openings are stitched together, without violating the MLC constraints, the number of segments used is reduced by 1. In FIG. 7D, 4 stitchings may be done, thus reducing the number of segments to 2 (see FIG. 7B).

It may be shown that it is sufficient to locally stitch together the field openings of the two selected delivery options for any two consecutive IMB columns, by computing a maximum cardinality matching between the two corresponding sets of intervals, with each interval representing exactly one selected field opening—the number of segments thus resulting is mathematically minimum with respect to the selected delivery options (with one delivery option for each IMB column), see D. Z. Chen, X.S. Hu, S. Luan, X. Wu, and C.X. Yu, Optimal terrain construction problems and applications in intensity-modulated radiation therapy, In Springer-Verlag, Lecture Notes in Computer Science, Proc. $10^{th}$ Annual European Symposium on Algorithms, volume 2461, pages 270-283, 2002; and D.Z. Chen, X. Hu, and X. Wu, Maximum red/blue interval matching with applications, In Proc. 7th Annual International Computing and Combinatorics Conf., pages 150-158, 2001, the entire contents and disclosures of which are hereby incorporated by reference. Every segment consists of a sequence of field openings thus stitched together, with one field opening from each of the selected delivery options for a consecutive list of IMB columns.

The above approach, for solving the Basic SLS segmentation problem, faces a major difficulty: the intensity profile of an IMB column often may be created by using any one of a large number of different delivery options, and any such delivery option may possibly be used by an optimal set of segments for creating that IMB. In fact, in the worst case, there may be up to N! different delivery options for an intensity profile, where N is the minimum number of field openings needed for creating the intensity profile, see S. Webb, Configuration options for intensity-modulated radiation therapy using multiple static fields shaped by a multileaf collimator, Phys. Med. Biol., 43:241-260, 1998; and C.X. Yu, Intensity-modulated arc therapy with dynamic multileaf collimation: An alternative to tomotherapy, Phys. Med. Biol., 40:1435-1449, 1995, the entire contents and disclosure of which is hereby incorporated by reference. For instance, the intensity profile in FIG. 8A has 3!=6 different delivery options in FIG. 8B.

A key idea of the present invention for resolving this difficulty is hinged on a geometric observation. To compute an optimal solution for the Bortfeld-Boyer segmentation problem, it is sufficient to use only a few special delivery options out of all possible delivery options. Being able to use dramatically fewer delivery options enables the algorithms/ software of the present invention to run very fast.

Another important concept is the notion of left and right MLC leaf positions of an intensity profile. Geometrically, an intensity profile is a functional curve f that is defined on an interval and consists of only vertical and horizontal edges, e.g., the thick solid curve in FIG. 8A. As one walks along such a curve f from left to right, each unit-length upward vertical edge segment in the walking direction is called a left leaf position (L-position), and each unit-length downward vertical edge segment is called a right leaf position (R-position). Note that a vertical edge of length L on f consists of L leaf positions (here, L is an integer). For convenience, the left leaf positions of an intensity profile are labeled as $L_i$'s, and the right leaf positions as $R_i$'s, in increasing order as its curve is traversed from left to right (see FIG. 8A). Clearly, the numbers of the L-positions and R-positions of each intensity profile are always the same.

Figure 8B:
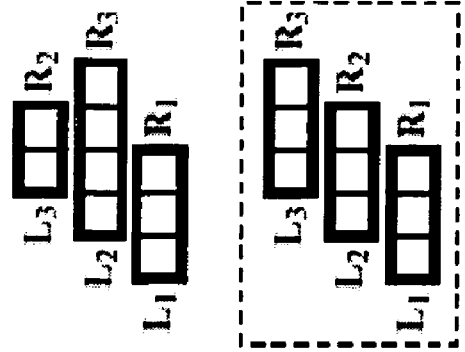
FIG. 8B shows the 3!=6 delivery options for the intensity profile in FIG. 8B where the delivery option enclosed by the dashed box is the only canonical delivery option.
Figure 8A:
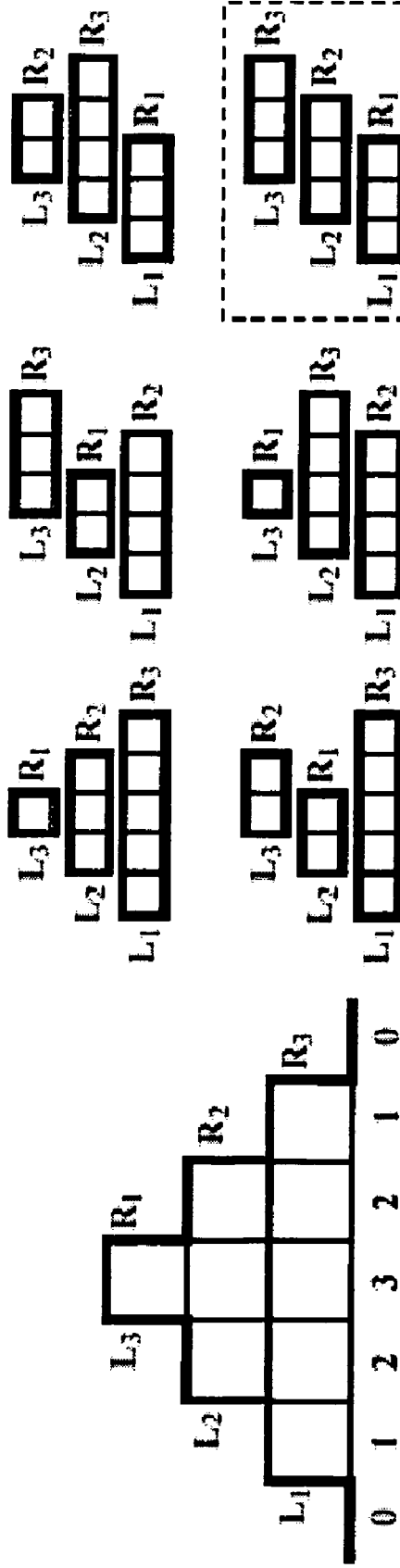
FIG. 8A shows an intensity profile, with the left leaf positions $L_1$, $L_2$ and $L_3$, and right leaf positions $R_1$, $R_2$ and $R_3$; and FIG.
Figure 10A:
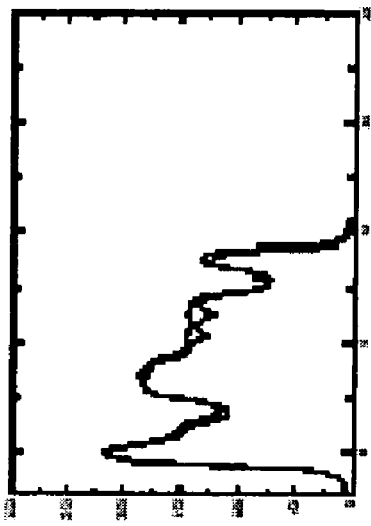
FIGS. 10A, 10B, 10C and 10D are graphs showing comparisons of the SLS (static leaf sequencing) and COR-VUS 4.0 dose profiles plotted using the RIT 113 Film Dosimetry System, where the vertical axis is for absolute doses in cGy, and the horizontal axis is for locations in cm, the CORVUS dose profiles are darker in color, and SLS dose profiles are in lighter in color, where the profiles in FIGS. 10A and 10B are orthogonal to the leaf motion direction, and where the profiles in FIGS. 10C and 10D are along the leaf motion direction.
Figure 10B:
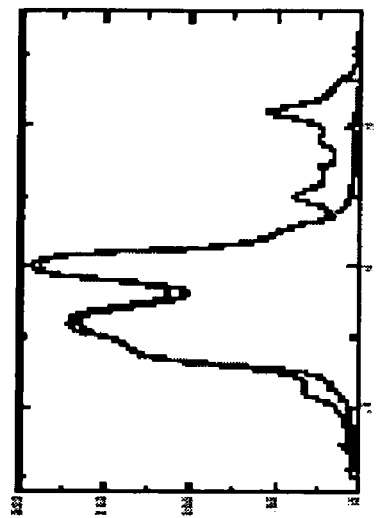
Figure 10C:
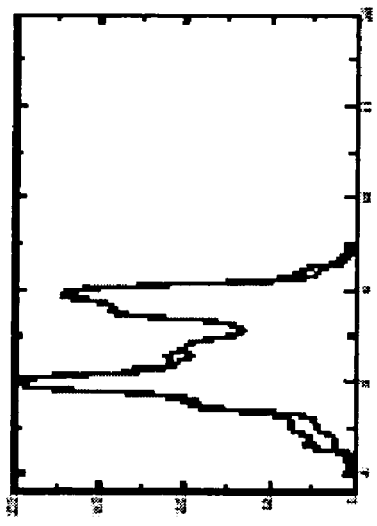
Figure 10D:
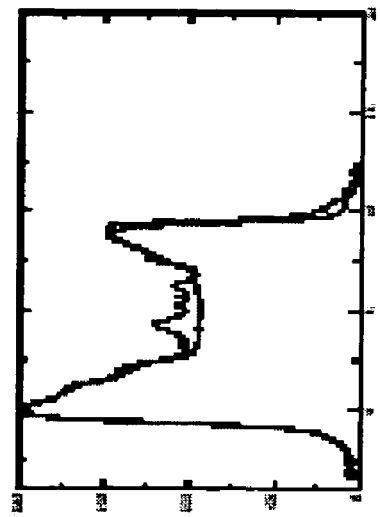

It is easy to see that every L- or R-position corresponds to exactly one endpoint of a field opening in any delivery option for an intensity profile (see FIG. 8B). That is, all L- and R-positions of the intensity profile correspond to some endpoints of the field openings of each of its delivery options. However, not every endpoint of the field openings of a delivery option necessarily corresponds to an L- or R-position of the intensity profile. That is, a field opening of a delivery option may have endpoints that need not be an L- or R-position of the intensity profile.

The left (resp., right) endpoint of a field opening that does not correspond to an L-position (resp., R-position) of its intensity profile is referred to as a left (resp., right) Steiner point. Steiner points may be specified on an intensity profile (for example, randomly) for defining field openings, with the numbers of specified left and right. Steiner points being the same. A delivery option with Steiner points has more field openings than a delivery option without Steiner points for an intensity profile. Note that the concept of Steiner points has also been described in Webb's paper, in which they are also called splits, see S. Webb, Configuration options for intensity-modulated radiation therapy using multiple static fields shaped by a multileaf collimator II: constraints and limitations on 2d, Phys. Med. Biol., 43:1481-1495, 1998, the entire contents and disclosure of which is hereby incorporated by reference.

The advantage of using delivery options with Steiner points is that the number of segments may be reduced. For example, the optimal solution in FIGS. 9C, 9D and 9E is obtained by breaking one of the field openings for the intensity profile of the middle IMB column of FIG. 9A at some Steiner points (FIG. 9C), thus enabling the bottom two segments in FIG. 9B to be connected into one segment and reducing the number of segments used.

The union of all left (resp., right) Steiner points (if any specified) and L-positions (resp., R-positions) on an intensity profile is referred to as the set of left (resp., right) field opening endpoints (FO-endpoints) of the intensity profile, which are still labeled as $L_i$'s (resp., $R_i$'s) in the left-to-right order. A delivery option for an intensity profile may be formed by a pairing between its left and right FO-endpoints, such that each left FO-endpoint is paired with exactly one right FO-endpoint that is to its right.

For a canonical delivery option, let $\{(L_{li},R_{ri})|1 \leq i \leq k\}$ be a delivery option based on a set S of FO-endpoints for an intensity profile, with k=|S|/2, such that each field opening $(L_{li},R_{ri})$ has a unit height. Then, the delivery option is said to be canonical if and only if for any two field openings $(L_{li},R_{ri})$ and $(L_{lj},R_{rj})$, i≠j, neither the closed interval $[x(L_{lj}), x(R_{ri})]$ is contained in the open interval $(x(L_{lj}), x(R_{rj}))$, nor the closed interval $[x(L_{lj}), x(R_{rj})]$ is contained in the open interval $(x(L_{li}), x(R_{ri}))$ (see FIG. 8B), where x(•) denotes the x-coordinate of an FO-endpoint.

According to an embodiment, the present invention has provided the following: (1) For any set of left and right FO-endpoints on an intensity profile, the canonical delivery option is unique and is $\{(L_i, R_i)|1 \leq i \leq k\}$; and (2) it is sufficient to use only the canonical delivery option, among all possible delivery options, for each set of left and right FO-endpoints of the intensity profile of every IMB column to compute a mathematically optimal set of segments for the Bortfeld-Boyer segmentation problem.

To highlight some of the key aspects of the present invention, an embodiment showing a version of an algorithm for solving the Bortfeld-Boyer segmentation problem is provided below. The assumption for this algorithm is that for the intensity profile of each IMB column, only one set of left and right FO-endpoints is used:

1. For the intensity profile of every IMB column, generate the unique canonical delivery option for the given set of FO-endpoints.

2. For every two consecutive IMB columns, compute a maximum matching between their canonical delivery options, see D.Z. Chen, X. Hu, and X. Wu, Maximum red/blue interval matching with applications, In Proc. 7th Annual International Computing and Combinatorics Conf., pages 150-158, 2001, the entire contents and disclosure of which is hereby incorporated by reference. Here, two field openings may be matched if they satisfy the no interdigitation constraint. One should note that the minimum leaf separation constraint has already been taken into account when a delivery option is generated. A maximum matching here corresponds to the stitching process discussed previously.

3. Extract the segments for the input IMB based on the matched field openings of the canonical delivery options in the increasing order of consecutive IMB columns.

Note that, for an IMB column of n entries (bixels), the number of possible locations for Steiner points is n−1. Since multiple Steiner points may be inserted at the same location, the number of possible sets for inserting m Steiner points onto the intensity profile is bounded by $O(n^m)$. Experience based on clinical data sets actually indicated that for IMRT planning, the number n is around 10 and the number m of Steiner points needed for producing an optimal set of segments is usually no bigger than 5. Hence, to compute an optimal set of segments for an IMB, one need only use a few tens of thousands of different sets of Steiner points to form the sets of FO-endpoints. For each such set of FO-endpoints, one only uses its unique canonical delivery option. In this way, using Steiner points in an algorithm of the present invention does not create a severe problem to the running time or processor demand. In fact, a program in accordance with an embodiment of the present invention runs in only a few minutes using the sets of FO-endpoints thus generated. Yet, the usage of Steiner points reduces the number of segments by 30% compared to not using Steiner points.

To distinguish the algorithm of the present invention used for the general 3-D segmentation problem, the following algorithm of the present invention for the Basic SLS segmentation problem may be referred to as the basic 3-D SLS:

1. Choose the number m of Steiner points for forming sets of FO-endpoints;

2. Generate the canonical delivery option for each set of FO-endpoints containing at most m Steiner points for the intensity profile of every IMB column;

3. Construct a directed graph G, such that each vertex of G corresponds to exactly one delivery option generated in Step 2;

4. For every two vertices of G corresponding to delivery options for the intensity profiles of any two consecutive IMB columns $C_j$ and $C_{j+1}$, put a directed edge from the vertex for column $C_j$ to the vertex for column $C_{j+1}$, and assign a weight to that edge based on a maximum matching between the two sets of field openings of the two corresponding delivery options (note that G thus constructed is acyclic); and 5. Generate a shortest path in G from a vertex of the first IMB column to a vertex of the last IMB column then specifies an optimal set of segments for the input IMB. (For descriptions of the shortest path problem and its algorithms, see T. H. Cormen, C. E. Leiserson, and R. L. Rivest, Introduction to Algorithms, pages 579-631, McGraw-Hill, 1998, the entire contents and disclosure of which is hereby incorporated by reference.) Note that when Steiner points are used, the intensity profile of each IMB column has many sets of FO-endpoints and thus many canonical delivery options (one canonical delivery option for each set of FO-endpoints). Then finding an optimal set of segments becomes a shortest path problem in G, see D. Z. Chen, X.S. Hu, S. Luan, X. Wu, and $C_{max}$. Yu, Optimal terrain construction problems and applications in intensity-modulated radiation therapy, In Springer-Verlag, Lecture Notes in Computer Science, Proc. $10^{th}$ Annual European Symposium on Algorithms, volume 2461, pages 270-283, 2002, the entire contents and disclosure of which is hereby incorporated by reference.

According to an embodiment of the present invention, the above basic 3-D SLS algorithm solves the Bortfeld-Boyer segmentation problem in a polynomial time of n if m is a constant (e.g., $m \leq 5$).

To be able to make use of the two algorithms of the present invention discussed above, the input 3-D IMB mountain should be partitioned into a set of nice sub-IMBs, such that each such sub-IMB may be handled optimally by one of these two algorithms, i.e., to use the 2-D SLS algorithm for the 2-D segmentation problem, a resulting sub-IMB must have a uniform height; to use the basic 3-D SLS algorithm for the Bortfeld-Boyer segmentation problem, the maximum height of such a sub-IMB should be reasonably small, for example, 7 or less. In some embodiments of the present invention, the sub-IMBs may be 5 or less.

A beamlet (an entry) of the input IMB with a value i is called a z-post of height i (z stands for the z-axis corresponding to intensity values). According to an embodiment of the present invention, the following scheme may be used to solve the general 3-D segmentation problem:

1. Let $I_{max}$ be the maximum intensity level of the IMB under consideration. If $I_{max}$ is small, e.g., no more than 5, then go to Step 5 and perform option (a) on the IMB;

2. Choose an intensity level d with $1 \leq d \leq I_{max}$;

3. Consider only z-posts of the IMB whose heights are at least d, i.e., for the time being, all z-posts lower than d are ignored. Cut each tall z-post (whose height is $\geq d$) at the level d, i.e., the part of the z-post at levels >d is ignored. (See FIG. 5B for an illustration, in which the chosen intensity level is d=4; the shaded portions of the IMB are the tall z-posts.) Observe that what is now left of the 3-D IMB mountain is a plateau consisting of z-posts of height exactly d;

4. Treat this plateau (of a uniform height d) as the input of a 2-D segmentation problem, and partition it into a minimum set of aperture shapes of height d using a 2-D SLS algorithm of the present invention; and 5. Remove the plateau from the 3-D IMB mountain, and recursively process the remaining IMB by using exactly one of the following two options, depending on the maximum height of the remaining IMB:

(a) If the maximum height of the remaining IMB is small, then apply the basic 3-D SLS algorithm of the present invention to obtain the segments for the IMB;

(b) Otherwise, repeat Steps 2-5 on the remaining IMB.

A key to the above scheme is how to choose an appropriate level d to form the plateaus (for producing a small set of segments for the input 3-D IMB mountain). There are several possible choices for d: a function of the maximum intensity level $$I_{max}\left(\text{e.g., } d = \left\lceil \frac{I_{max}}{2} \right\rceil \right),$$

a function of the volume of the resulting plateau, a random choice, etc. Experiments on these choices of d using various real medical data sets showed that different choices of d give good results for different types of data sets. To obtain the best quality output, our general 3-D SLS algorithm combines various ways of choosing d in a mixed fashion referred to as a mixed partitioning method. Specifically, in the mixed partitioning method, every time Step 2 of the above scheme is performed, each of the above-identified ways to choose d may be used, and the algorithm, based on every chosen value of d, is carried out recursively on the remaining IMB. At the end, the 3-D SLS algorithm of the present invention selects the best overall result. The number of different ways of choosing d discussed herein is only four, although, based on the characteristics of the intensity maps in hand, one may develop and include/exclude any partitioning methods into/from this scheme.

The four methods of choosing d used in the general 3-D SLS algorithm/software of the present invention are as follows:

(1) Xia and Verhey's partitioning method: For the IMB under consideration, choose the power of 2 that is closest to $$\frac{I_{max}}{2} \text{ (i.e., } d = 2^i, \text{ where } i = \text{Int}(\log_2(I_{max})) - 1);$$

(2) Que's half cutting method, see W. Que, Comparison of algorithms for multileaf collimator field segmentation, Med. Phys., 26:2390-2396, 1999, the entire contents and disclosure of which is hereby incorporated by reference:

$$d = \left\lceil \frac{I_{max}}{2} \right\rceil;$$

(3) The maximum volume method: d is chosen such that the volume of the resulting plateau is maximized; and/or (4) The slice method, see L. D. Potter, S. X. Chang, T. J. Cullip, and A. C. Siochi, A quality and efficiency analysis of the IMFAST™ segmentation algorithm in head and neck step & shoot IMRT treatments, Med. Phys., 29 (3):275-283, 2002; and R. Svensson, P. Kallman, and A. Brahme, An analytical solution for the dynamic control of multileaf collimation, Phys. Med. Biol., 39:37-61, 1994, the entire contents and disclosures of which are hereby incorporated by reference: Let d be the smallest positive entry of the IMB.

The program for the general 3-D SLS algorithm of the present invention based on the above mixed partitioning method usually runs in only a few minutes. Yet, the mixed partitioning method helps produce 10%-20% fewer segments.

To further study the effectiveness and performance of the 3-D SLS algorithm of the present invention, it was implemented using the C programming language on a Linux workstation. The software package is named SLS. SLS is designed to use the CORVUS intensity maps as input, and the ELEKTA Precise Treatment System™ (RT Desktop) as the target delivery machine.

A typical IMRT planning process with SLS is carried out using the following major steps:

1. Generate the CORVUS prescriptions and intensity maps;

2. Import the CORVUS intensity maps and compute the SLS aperture shapes (segments) for these intensity maps;

3. Import the CORVUS prescription files and compute the monitor units (MU) for the SLS aperture shapes. For the MU computation, two different methods are used: a full blown Monte Carlo based dosage calculation program and a much simpler discrete intensity map guided MU calculation program, see S. A. Naqvi, M. Earl, and D. Shepard, Convolution/superposition using the Monte Carlo method, submitted to Phys. Med. Biol., 2003, the entire contents and disclosure of which is hereby incorporated by reference. The underlying idea of using a Monte Carlo based MU calculation is to make sure that the two leaf sequences (SLS and CORVUS) match each other in 3-D dose, by adjusting the amount of monitor units prescribed. The idea of an intensity map guided MU calculation is to guarantee that the SLS prescriptions match the CORVUS prescriptions in beamlet intensities. Using these two methods for MU calculation enhances the error tolerance of our SLS software; and 4. Encode and transfer the SLS prescriptions, by using a DICOM RT protocol, to the radiation delivery machines. For this step, a DICOM encoding and transferring software was developed using the MergeCOM-3™ Advanced Integrator's Tool Kit for UNIX of Red Hat Linux systems.

After the SLS software package was developed, experiments and comparisons were conducted between SLS and two popular segmentation algorithms/software: the CORVUS inverse planning system (the 4.0 and 5.0 versions) and Xia and Verhey's: segmentation algorithm. In general, the results indicated the following:

1. The SLS software was implemented correctly;

2. The treatment plans produced by SLS are feasible for patient treatments; and

3. The SLS plans have a significantly smaller number of segments and therefore may be delivered in a much shorter treatment time.

Comparisons were conducted between SLS software according to the present invention and the CORVUS 4.0 planning system used in the Department of Radiation Oncology, University of Maryland School of Medicine. A main objective of this study was to verify the clinical feasibility of the SLS software package. Hence, the comparisons were largely focused on whether the plans computed by SLS match the original CORVUS plans in 3-D dose.

Table I (below) gives some comparison results, which show that SLS significantly outperforms CORVUS 4.0 in terms of the number of segments computed. In Table I, the numbers of segments computed by SLS are up to 80% less than CORVUS 4.0. As a result, the treatment time has also been improved substantially by the SLS plans. For example, for the pancreatic case in Table I, the treatment time was shortened from 72 minutes for the CORVUS 4.0 plans to 25 minutes for the SLS plans. Note that the treatment time was measured on an ELEKTA linac system, and should be accelerated on SIEMENS and VARIAN machines. Even for machines without a large inter-segment delay as on ELEKTA, the substantial reduction of the number of segments used, e.g., from 381 to 84 as the pancreas case in Table I, should significantly shorten the treatment time.

Generally speaking, the dose distributions created by SLS plans and CORVUS 4.0 plans for the same set of intensity maps are very similar. The difference between the isodose lines is within 2 mm, and the difference of doses measured by ion chamber at the isocenters is within 3%. Below, a pancreatic case is used as an example to show the similarities between the SLS plans and the original CORVUS plans in terms of their dose distributions.

Figure 11B:
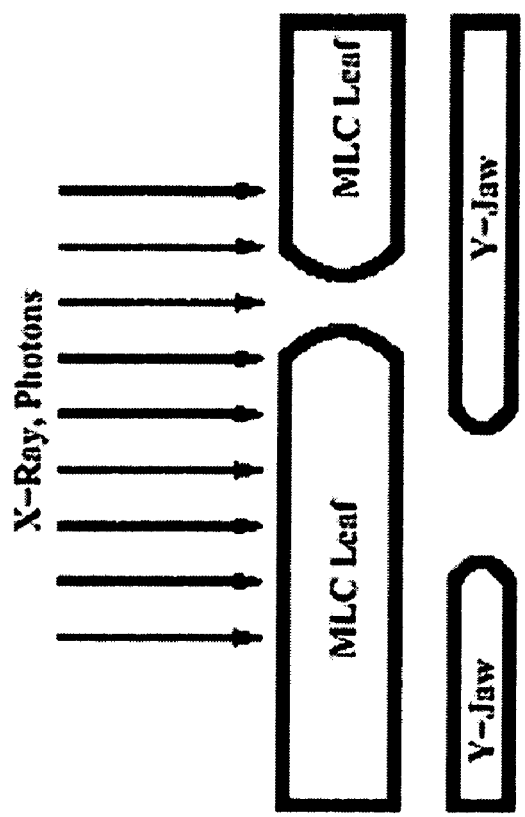
FIGS. 11A and 11B illustrate how MLC leaves and Y-jaws are used for blocking radiation, with FIG. 11A showing CORVUS 4.0, and FIG. 11B showing SLS in accordance with an embodiment of the present invention.
Figure 11A:
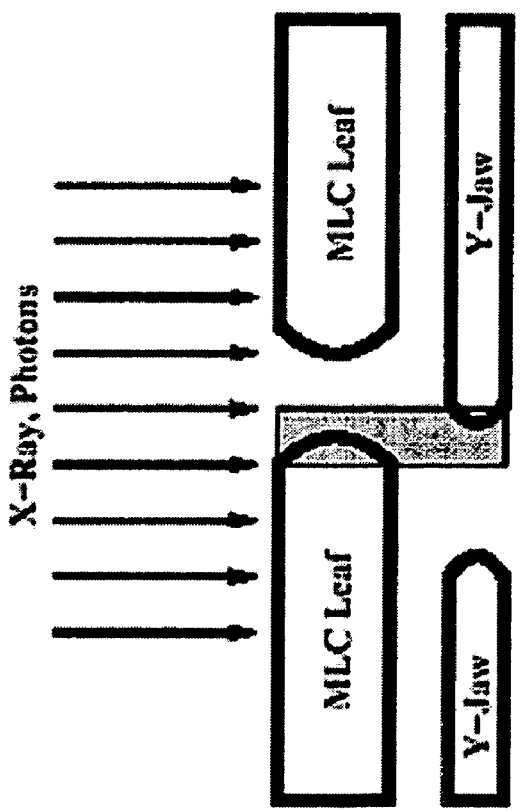

FIG. 10 shows the dose profiles of the CORVUS 4.0 and SLS plans for a pancreatic case. As may be seen from FIG. 10, these dose profiles are very similar. The bigger differences exhibited which are close to the left and right ends of the dose profiles are due to the leakage of the CORVUS 4.0 plans. These differences are outside the beams, and are caused by the way that CORVUS 4.0 uses the MLC leaves and backup diaphragms to block radiation. Note that on the ELEKTA linac system, MLC leaves cannot be completely closed and must maintain a minimum leaf separation distance. Hence, to achieve the effect of fully blocking the radiation through a pair of MLC leaves, the backup diaphragms are brought in. The backup diaphragms are also referred to as the X- and Y-jaws (the Y-jaws have a 10% leakage). The way the Y-jaws are used for blocking leaf openings in CORVUS 4.0 is shown in FIG. 11A. Basically, CORVUS 4.0 assumes that the Y-jaws and MLC leaves are "perfect" blockers. In contrast, the way the Y-jaws are used for blocking leaf openings in SLS is shown in FIG. 1B. The shaded area in FIG. 11A indicates the place in which most leakage occurs. As may be seen, CORVUS 4.0 has more leakage, especially around the boundaries of the beams.

Figure 12A:
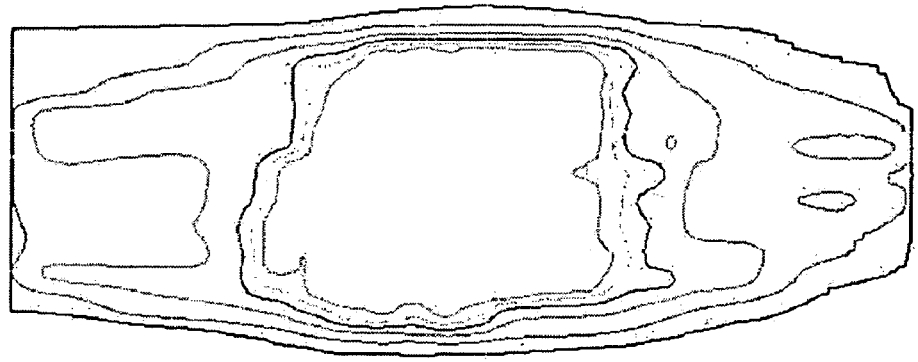
FIGS. 12A, 12B and 12C show comparisons of dose distributions on the coronal plane with FIG. 12A showing the CORVUS plan isodose lines: 90%, 75%, 60%, 40%, 20% and 10%, FIG. 12B showing the SLS plan isodose lines: 90%, 75%, 60%, 40%, 20% and 10%.
Figure 12B:
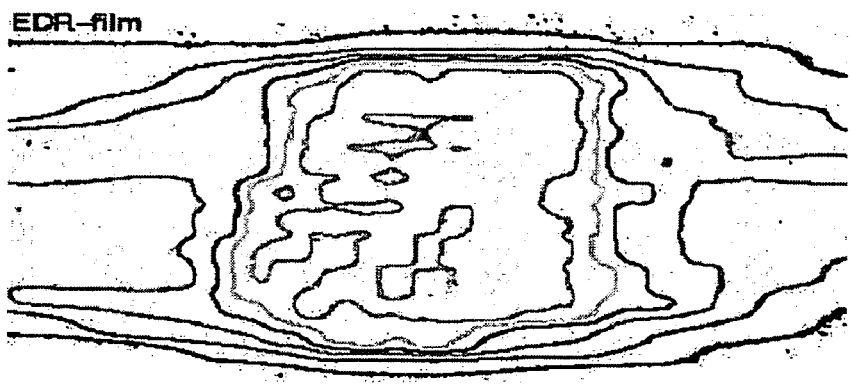
Figure 12C:
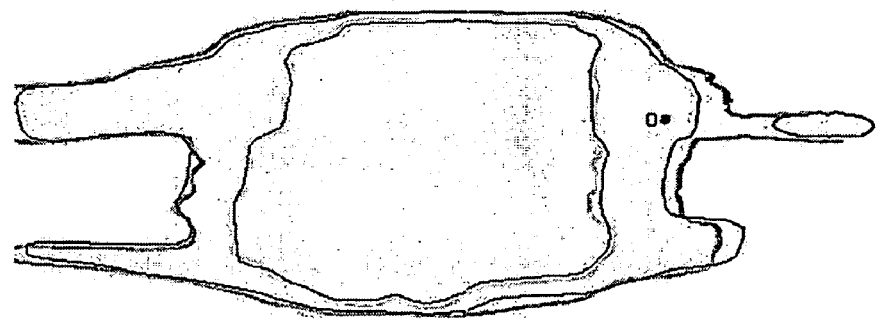

FIG. 12 shows the CORVUS 4.0 and SLS dose distributions and the comparisons on the coronal plane for the same pancreatic case. In FIG. 12, the isodose lines of these two types of plans are very similar. Based on measurements, the difference between the two 75% lines is within 2 mm.

Since the dose measured by films has a 5%-10% error, an ion chamber measurement was also performed at the isocenters. In this case, the dose measured for the SLS plan is 183 cGy, while the CORVUS 4.0 prescribed dose is 178 cGy. The difference is within 3%.

Comparisons were also conducted between SLS and CORVUS 5.0 as well as Xia and Verhey's segmentation algorithm. The focus of these comparisons was primarily on the number of segments computed by each algorithm/software.

CORVUS 5.0 is the latest version of the CORVUS planning system. SLS was also compared with Xia and Verhey's algorithm because their algorithm has been coded by many people and has been used as a generally accepted benchmark program. Xia and Verhey's algorithm was implemented with the ELEKTA constraints based on the reducing level method.

Table II (below) gives the comparison results. Since the SLS software does not address the tongue and groove correction, for a fair comparison, CORVUS 5.0 results were included both with the leakage correction and without the leakage correction. As shown by Table II, SLS outperforms CORVUS 5.0 by a factor of about 40% (31% when the leakage correction is turned off) in terms of the number of segments computed, and outperforms Xia and Verhey's algorithm by a factor of about 33%. On all the cases, SLS performs better than CORVUS 5.0 and Xia and Verhey's algorithm in various degrees.

TABLE I

SLS v. CORVUS 4.0 (with leakage correction)

| | Number of IMBs | $I_{max}$ | Field size (in cm) | Number of segments CORVUS 4.0 | SLS | Number of MUs CORVUS 4.0 | SLS |
|---|---|---|---|---|---|---|---|
| Head and Neck | 5 | 5 | 6 × 6 | 143 | 32 | 1314 | 660 |
| Thyroma | 7 | 5 | 10 × 9 | 235 | 83 | 1808 | 1101 |
| Pancreas | 7 | 5 | 10 × 12 | 381 | 84 | 2752 | 1491 |
| Prostate | 7 | 5 | 9 × 9 | 281 | 57 | 2213 | 1416 |

TABLE II

SLS v. CORVUS 5.0 (with and without leakage correction) and Xia and Verhey's algorithm

| | | | | Number of segments | | | |
|---|---|---|---|---|---|---|---|
| | | | | CORVUS 5.0 | | | |
| | Number of IMBs | Maximum intensity level | Field size (in cm) | with leakage correction | without leakage correction | Xia and Verhey's | SLS |
| Brain | 5 | 5 | 2 × 3 | 22 | 24 | 23 | 17 |
| Head & Neck | 6 | 10 | 4 × 5 | 64 | 65 | 72 | 63 |
| | 7 | 5 | 16 × 15 | 262 | 215 | 216 | 133 |
| Prostate | 5 | 5 | 7 × 8 | 72 | 61 | 63 | 39 |

The present invention provides a new segmentation algorithm, called SLS, for step-and-shoot IMRT delivery. Unlike previous segmentation approaches, SLS is based on graph algorithmic techniques in computer science, and exploits the geometric nature of the problem. The implementation and experiments of SLS on an ELEKTA linac system showed that the SLS software substantially outperforms CORVUS (versions 4.0 and 5.0) and Xia and Verhey's algorithm in terms of minimizing the number of MLC aperture shapes and shortening the treatment time. Film and ion chamber measurements proved that the SLS plans match well with the CORVUS commercial planning system in 3-D composite dose and hence paved the way for the clinical applications of SLS.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method comprising the following steps:
  (a) recursively partitioning an intensity modulated beam into plateaus;
  (b) partitioning the plateaus into segments; and
  (p) administering radiation therapy using the segments; and wherein the method further comprises:
  (c) constructing a directed graph based on the plateaus;
  (d) determining a maximum flow in the directed graph; and
  (e) extracting the segments from the directed graph based on the maximum flow determined in step (d) to thereby partition the plateaus; and
  wherein step (c) comprises the following steps:
  (f) constructing a directed graph based on intensity modulated beam grids of the plateaus of an intensity modulated beam, wherein vertices of the directed graph include all intersection points of the intensity modulated beam grids of the plateaus that are either part of a peak or an interior of a polygon corresponding to the intensity modulated beam, and wherein the edges of the directed graph include those edges of the plateaus whose end points are graph vertices in the directed graph;
  (g) for all graph vertices corresponding to the same peak direction, adding either a source vertex or sink vertex to the directed graph;
  (h) adding edges to the directed graph from the source vertex or sink vertex to respective peak vertices; and
  (i) assigning a unit flow capacity to each graph vertex and edge of the directed graph.

2. The method of claim 1, wherein step (e) comprises the following steps:
  (j) extracting connections between a left peak and a right peak of the polygon based on the maximum flow;
  (k) eliminating any remaining unconnected peaks; and
  (l) extracting resulting segments from the directed graph to thereby partition the plateaus.

3. The method of claim 1, wherein for an edge involving a left peak vertex, the direction of the edge is away from the left peak.

4. The method of claim 1, wherein for an edge involving a right peak vertex, the direction of the edge is toward the right peak.

5. The method of claim 1, wherein the direction of a horizontal edge that does not involve any peak vertex is from left to right.

6. The method of claim 1, wherein the direction of a vertical edge that does not involve a peak vertex is bidirectional.

7. The method of claim 1, wherein, for all left peak vertices, a source vertex is added to the directed graph.

8. The method of claim 1, wherein, for all right peak vertices, a sink vertex is added to the directed graph.

9. The method of claim 1, wherein the maximum flow in the directed graph yields a maximum set of mutually disjoint paths.

10. A method comprising the following steps:
  (a) recursively partitioning an intensity modulated beam into plateaus;
  (b) partitioning the plateaus into segments; and
  (p) administering radiation therapy using the segments; and
  wherein the method further comprises:
  (c) choosing an intensity level d wherein, $1 \leq d \leq I_{max}$, wherein $I_{max}$ is the maximum intensity level of the intensity modulated beam;
  (d) selecting all z-posts having a height of at least d to form a set of selected z-posts;
  (e) cutting each selected z-post whose height is $\geq d$ at level d to form a plateau of z-posts of height d;
  (f) removing the plateau of z-posts from the intensity modulated beam; and
  (g) recursively partitioning any remaining portion of the intensity modulated beam until there is no remaining portion of the intensity modulated beam.

11. The method of claim 10, wherein step (g) comprises repeating steps (c), (d), (e) and (f) on any remaining portion of the intensity modulated beam until there is no remaining portion of the intensity modulated beam.

12. The method of claim 10, wherein d is a function of the maximum intensity level $I_{max}$.

13. The method of claim 10, wherein $$d = \left\lceil \frac{I_{max}}{2} \right\rceil.$$

14. The method of claim 10, wherein d is based on the volume of the plateau of z-posts.

15. The method of claim 10, wherein $d=2^i$, where i=Int $(\log_2(I_{max}))-1$.

16. The method of claim 10, wherein d has a value such that the volume of the plateau of z-posts is maximized.

17. The method of claim 10, wherein d is determined by the slice method.

18. A method comprising the following steps:
  (a) recursively partitioning an intensity modulated beam into plateaus;
  (b) partitioning the plateaus into segments;
  (p) administering radiation therapy using the segments; and
  wherein step (a) further comprises: partitioning the intensity modulated beam into a sub-IMB, and wherein the method further comprises the following step: (c) partitioning the sub-IMB into segments; and wherein step (c) comprises the following steps:
(d) generating a canonical delivery option for each set of field opening endpoints for a plurality of intensity modulated beam columns of the sub-IMB;
(e) for every two consecutive intensity modulated beam columns, determining a maximum matching between the canonical delivery options of the intensity modulated beam columns; and
(f) extracting the segments for the sub-IMB based on the matched field openings of the canonical delivery options in an increasing order of consecutive intensity modulated beam columns to thereby partition the sub-IMB.

19. The method of claim 18, wherein in step (d) only one set of left and right field opening endpoints is generated for each intensity beam column.

20. The method of claim 18, wherein in step (d) more than one set of left and right field opening endpoints is generated for each intensity beam column.

21. The method of claim 18, wherein the matched field openings have no interdigitation.

22. The method of claim 18, wherein the method further comprises choosing a number m of Steiner points for forming the sets of field opening endpoints, and wherein each unique canonical delivery option contains at most m Steiner points for each set of field opening endpoints.

23. A method comprising the following steps:
(a) generating a canonical delivery option for each set of field opening endpoints for a plurality of intensity modulated beam columns of an IMB;
(b) for every two consecutive intensity modulated beam columns, determining a maximum matching between the canonical delivery options of the intensity modulated beam columns; and
(c) extracting the segments for the IMB based on the matched field openings of the canonical delivery options in an increasing order of consecutive intensity modulated beam columns to thereby partition the IMB; and
(d) administering radiation therapy using the segments.

* * * * *